(12) United States Patent
Pass et al.

(10) Patent No.: US 7,901,896 B2
(45) Date of Patent: Mar. 8, 2011

(54) ASBESTOS EXPOSURE, PLEURAL MESOTHELIOMA, AND OSTEOPONTIN LEVELS

(75) Inventors: Harvey I. Pass, New York, NY (US); Anil Wali, Detroit, MI (US)

(73) Assignee: Wayne State University, Detroit, MI (US)

( * ) Notice: Subject to any disclaimer, the term of this patent is extended or adjusted under 35 U.S.C. 154(b) by 204 days.

(21) Appl. No.: 11/996,275

(22) PCT Filed: Jul. 19, 2006

(86) PCT No.: PCT/US2006/028118
§ 371 (c)(1),
(2), (4) Date: Sep. 22, 2008

(87) PCT Pub. No.: WO2007/013949
PCT Pub. Date: Feb. 1, 2007

(65) Prior Publication Data
US 2009/0311721 A1     Dec. 17, 2009

Related U.S. Application Data

(60) Provisional application No. 60/701,266, filed on Jul. 21, 2005.

(51) Int. Cl.
*G01N 33/53* (2006.01)
(52) U.S. Cl. .......................... 435/7.1; 436/518
(58) Field of Classification Search ................ None
See application file for complete search history.

(56) References Cited

U.S. PATENT DOCUMENTS

| | | | |
|---|---|---|---|
| 4,569,788 | A | 2/1986 | Mulshine |
| 6,902,890 | B1 | 6/2005 | Recipon |
| 2003/0044862 | A1 | 3/2003 | Giaccia |

FOREIGN PATENT DOCUMENTS

| | | |
|---|---|---|
| WO | 02/24956 | 3/2002 |

OTHER PUBLICATIONS

Paleari et al. Int Biol. Markers 2009 vol. 24, p. 112-117.*
Pass et al., Gene Expression Profiles Predict Survival and Progression of Pleural Mesothelioma, Clin. Cancer Res. 10(3):849-859, 2004.
Fedarko et al., Elevated Serum Bone Sialoprotein and Osteopontin in Colon, Breast, Prostate, and Lung Cancer, Clin. Cancer Res. 7(12):4060-4066, 2001.
Singhal et al., Elevated Plasma Osteopontin in Metastatic Breast Cancer Associated With Increased Tumor Burden and Decreased Survival, Clin. Cancer Res. 3 (4):605-611, 1997.
Denhardt, Osteopontin Expression Correlates With Melanoma Invasion, J. Invest. Dermatol. 124:xvi-xviii, 2005.
Ding et al., Expression and Clinical Significance of Osteopontin in Colorectal Cancer and Liver Metastatic Tissues, Zhonghua Wai Ke Za Zhi 40(10):773-775, 2002.
Ue et al., Co-Expression of Osteopontin and CD44v9 in Gastric Cancer, Int. J. Cancer 79:127-132, 1998.
Schorge et al., Osteopontin As an Adjunct to CA125 in Detecting Recurrent Ovarian Cancer, Clin. Cancer Res. 10:3474-3478, 2004.
Brakora et al, Utility of Osteopontin As a Biomarker in Recurrent Epithelial Ovarian Cancer, Gynecol. Oncol. 93(2):361-365, 2004.
Kim et al., Osteopontin As a Potential Diagnostic Biomarker for Ovarian Cancer, JAMA 287(13):1671-1679, 2002.
Wai et al., The Role of Osteopontin in Tumor Metastasis, J. Surg. Res. 121 (2):228-241, 2004.
Sandhu et al., mRNA Expression Patterns in Different Stages of Asbestos-Induced Carcinogenesis in Rats, Carcinogenesis 21(5):1023-1029, 2000.
Denhardt and Guo, Osteopontin: A Protein With Diverse Functions, FASEB J. 7:1475-82, 1993.
Denhardt et al., Osteopontin: Role in Cell Signalling and Adhesion, Ann. NY Acad. Sci. 760:1-382, 1995.
Coppola et al., Correlation of Osteopontin Protein Expression and Pathological Stage Across a Wide Variety of Tumor Histologies, Clin. Cancer Res. 10:184-190, 2004.
Schneider et al., Osteopontin But Not Osteonectin Messenger RNA Expression Is a Prognostic Marker in Curatively Resected Non-Small Cell Lung Cancer, Clin. Cancer Res. 25 10 (5):1588-1596, 2004.
Koopmann et al., Evaluation of Osteopontin As Biomarker for Pancreatic Adenocarcinoma, Cancer Epidemiol. Biomarkers Prev. 13(3):487-491, 2004.
Martinetti et al., Osteoprotegerin and Osteopontin Serum Values in Postmenopausal Advanced Breast Cancer Patients Treated With Anastrozole, Endocr. Relat. Cancer 11 (4):771-779, 2004.
McIntosh et al., Combining CA 125 and SMR Serum Markers for Diagnosis and Early Detection of Ovarian Carcinoma, Gynecol Oncol. 95(1):9-15, 2004.
Pass et al., Preoperative Tumor Volume Is Associated With Outcome in Malignant Pleural Mesothelioma, J. Thorac. Cardiovasc. Surg. 115(2):310-317, 1998.
Rusch et al., Important Prognostic Factors in Patients With Malignant Pleural Mesothelioma, Managed Surgically, Ann. Thorac. Surg. 68(5): 1799-1804, 1999.
Rusch et al., The Importance of Surgical Staging in the Treatment of Malignant Pleural Mesothelioma, J. Thorac. Cardiovasc. Surg. 111(4):815-825, 1996.
Duffy, Michael J., "Carcinoembryonic Antigen as a Marker for Colorectal Cancer: Is is clinically useful?" Clinical Chemistry, vol. 47, No. 4, Apr. 2001, pp. 624-630.

* cited by examiner

*Primary Examiner* — Jacob Cheu
(74) *Attorney, Agent, or Firm* — C. Rachal Winger; K&L Gates LLP

(57) ABSTRACT

The present invention provides diagnostic methods based on the levels of osteopontin.

9 Claims, 7 Drawing Sheets

ASBESTOS EXPOSURE, PLEURAL MESOTHELIOMA, AND OSTEOPONTIN LEVELS

BACKGROUND

1. Technical Field

The present disclosure relates to occurrence of osteopontin in tissues and fluids of subjects afflicted with pleural mesothelioma, and discloses serum osteopontin levels in three populations: asbestos-exposed subjects without malignancy, unexposed subjects without malignancy, and asbestos-exposed subjects with pleural mesothelioma.

2. Related Art

Pleural mesothelioma is an asbestos-related malignancy with a median survival of 8-18 months (Martino D et al., Clin Lung Cancer 2004; 5(5):290-298). Retrospective studies of small numbers of pleural mesothelioma patients have attempted to define biomarkers that predate symptoms in a population at high risk for pleural mesothelioma. These markers include tissue polypeptide antigen, carcinoembryonic antigen, hyaluronic acid and ferritin, hyaluronic acid alone, cytokeratins including Cyfra 21™, CA-125, and mesothelin related protein (SMRP) (Ebert W, et al., Anticancer Res 1997; 17(4B):2875-2878; Pettersson T, et al. Chest 1988; 94(5):1037-1039; Frebourg T, et al. Cancer 1987; 59(12):2104-2107; Roboz J, et al. J Natl Cancer Inst 1989; 81(12):924-928; Chiu B, et al, Cancer 1984; 54(10):2195-2199; Boersma A, et al. Bull Physiopathol Respir (Nancy) 1980; 16(1):41-45; Hellstrom PE, et al. Scand J Respir Dis 1977; 58(2):97-102; Thylen A, et al. Cancer 2001; 92(5):1224-1230; Pluygers E, et al. Cancer Prev 1992; 1(2):129-138; Lee Y C, et al. Aust N Z J Med 1999; 29(6):765-769; Paganuzzi M, et al. Chest 2001; 119(4):1138-1142; Schouwink H, et al. Lung Cancer 1999; 25(1):25-32; Marukawa M, et al. Acta Med Okayama 1998; 52(2):119-123; Bonfrer J M, et al. Anticancer Res 1997; 17(4B):2971-2973; Almudevar B E, et al. Histopathology 1997; 31(3):267-273; Robinson B W, et al. Lancet 2003; 362(9396): 1612-1616).

The lifetime risk for pleural mesothelioma in an asbestos-exposed population is 4.5-10%. Workers at risk for high exposure include miners, factory workers, carpenters, electricians, ship fitters, ship electricians, boilermakers, insulation manufacturers, railroad workers, gas mask manufacturers, and pipe insulators (Roggli V L, et al. Ultrastruct Pathol 2002; 26(2): 55-65). It has been estimated that as many as 7,500,000 construction workers in the United States have used asbestos construction materials for fireproofing buildings, acoustic control, duct work and pipe and boiler instillation (Schottenfeld D, et al. Cancer Epidemiology and Prevention. Philadelphia: W.B. Saunders Co., 1982). Moreover, asbestos is still a hazard for an estimated 1.3 million workers in the construction industry in the United States and for workers involved in maintenance of building and equipment (U.S. Department of Labor OSaHA. Safety and Health Topics: Asbestos. 2003).

At present, there are no economically feasible, validated modalities to screen all these individuals potentially at risk when the estimated number of new cases of mesothelioma in the United States per year is only 2500-3000 (age adjusted incidence of 2/100,000) (Weill H, et al. Occup Environ Med 2004; 61(5):438-441). However, the incidence of mesothelioma is rising in and outside the United States, including Canada and Australia. Median survival in pleural mesothelioma is 9-12 months from diagnosis; in advanced cases, resection of the tumor can prolong survival for about three months. Patients with stage IA disease, however, can survive 5 or more years if the tumor is promptly resected. Unfortunately, the difficulty in detecting early disease means that less than 5% of patients with pleural mesothelioma present in stage IA; in fact 85% of patients first present once they are exhibiting symptoms of the disease. Hence, a marker or series of biomarkers that can predict the development of mesothelioma or detect pleural mesothelioma in its early stages in asbestos-exposed populations would be of considerable value.

BRIEF SUMMARY

The present disclosure relates to the use of osteopontin as a noninvasive marker for mesothelioma in human subjects. Osteopontin levels are elevated in serum of patients with mesothelioma, and measurement of these levels can be carried out conveniently for the purpose of diagnosis, prognosis and therapy.

In one of its aspects, the disclosure provides a method of diagnosing mesothelioma by detecting a level of osteopontin in a bodily fluid or other biological sample of a patient, such as blood, serum, sputum, bronchial or alveolar lavage, a lung aspirate, a pleural fluid sample, or another sample derived from or contacted with lung tissue, and comparing the level with a predetermined value or values or with a comparable sample obtained from another patient of known mesothelioma status.

In yet another aspect, the disclosure provides a method for monitoring the response of a mesothelioma to radiation or chemotherapy, comprising diagnosing the mesothelioma, and measuring osteopontin levels before, during and/or after the radiation or chemotherapy treatment.

In still another aspect, the disclosure provides a method of monitoring the response of a patient to tumor therapy, comprising determining a level of osteopontin in a bodily fluid obtained from the patient prior to therapy, and at various times during and after therapy, and comparing the level to one another or to a predetermined value or values that are indicative of the presence of mesothelioma.

The disclosure also provides a kit containing at least one binding agent for detecting osteopontin and calibration means for comparing the level of osteopontin with a predetermined value or values corresponding to presence of mesothelioma. Examples of suitable calibration means include standardized osteopontin in amounts corresponding to a predetermined value or range of values, instructions for using the kit, and a description of osteopontin levels in various bodily fluids corresponding to negative and positive results for mesothelioma.

DESCRIPTION OF THE FIGURES

FIG. 1A shows the median survivals for the Stage I (solid line), Stage II (long dashes), and Stage III (short dashes) patients. FIG. 1B shows the median time to progression for the Stage I (solid line), Stage II (long dashes), and Stage III (short dashes) patients.

FIG. 3A illustrates osteopontin levels in asbestos exposed subjects (E) and age-matched controls (U) for subjects younger than 50, between the ages of 50 and 60, or older than 60 years (y). FIG. 3B illustrates osteopontin levels in asbestos exposed subjects and age-matched controls by gender: (F) female and (M) male. FIG. 3C illustrates the level of osteopontin with years (y) of asbestos exposure. FIG. 3D illustrates the degree of radiographic abnormality in relation to osteopontin levels.

FIG. 4A illustrates all 76 mesotheliomas versus 69 asbestos exposed. FIG. 4B illustrates the high sensitivity for early detection of mesothelioma at a cutoff level of 10.9 ng/ml. FIG. 4C illustrates the cut-off for minimization of total classification error. FIG. 4D illustrates stage I mesotheliomas versus asbestos exposed subjects. FIG. 4E illustrates high sensitivity for early detection of Stage I mesothelioma versus asbestos exposed subjects at cutoff level of 9.5 ng/ml. FIG. 4F illustrates the cut-off for minimization of total classification error for Stage I versus asbestos exposed.

DETAILED DESCRIPTION

Figure 1A:
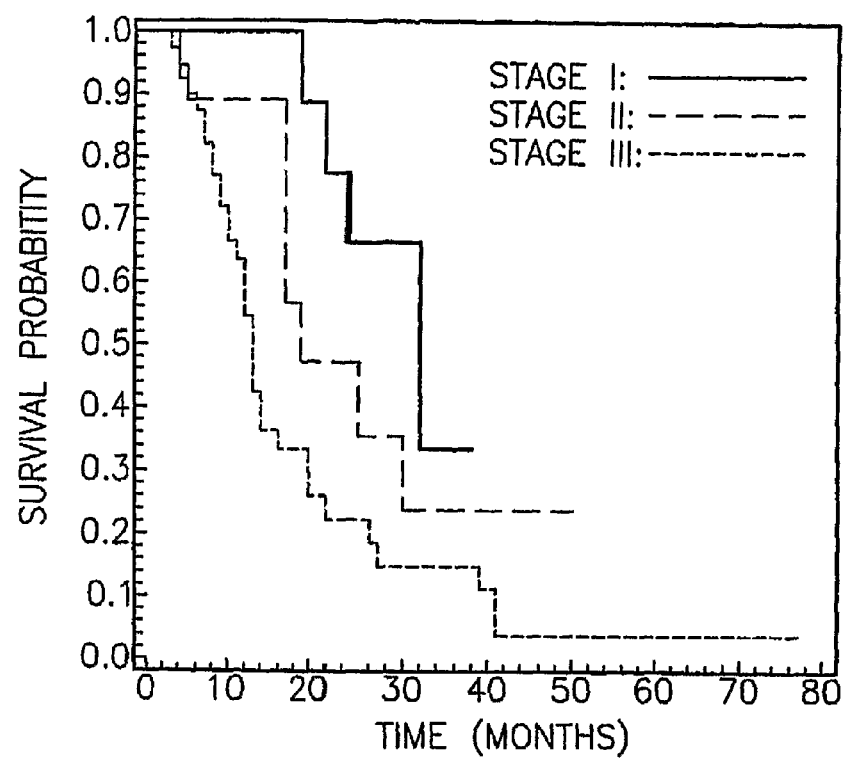
FIGS. 1A and 1B are graphs that illustrate validation of the natural history for the test set of 76 mesotheliomas.

The present disclosure provides new evidence that osteopontin is a useful biomarker for mesothelioma, including pleural mesothelioma, and more specifically provides comparison of serum levels of osteopontin in a cohort of patients with asbestos-related non-malignant disease (hereafter called the asbestos-exposed group) with preoperative levels in surgically treated pleural mesothelioma patients. Populations with asbestos-related nonmalignant disease are an ideal cohort in which to study biomarkers for the early detection of pleural mesothelioma, because they are at a high risk for development of the tumor; they have had a measurable, identifiable exposure to the carcinogen; reside in defined and well studied geographical regions; and comply in long-term follow-up studies (Cullen M R et al., Am J Epidemiol 2005; 161(3):260-270).

In prior work, we used gene expression arrays to predict survival and recurrence patterns in pleural mesothelioma (Pass H I, et al. Clin Cancer Res 2004; 10(3):849-859) and to seek markers that would be useful for screening and diagnosis of pleural mesothelioma. The most promising biomarker was osteopontin, a glycoprotein that is overexpressed in lung, breast, melanoma, colorectal cancer, gastric cancer, and ovarian cancer (Fedarko N S, et al. Clin Cancer Res 2001; 7(12): 4060-4066; Singhal H, et al. Clin Cancer Res 1997; 3(4):605-611; Denhardt D. J Invest Dermatol 2005; 124(5):xvi-xviii; Ding L, et al. Zhonghua Wai Ke Za Zhi 2002; 40(10):773-775; Ue T, et al. Int J Cancer 1998; 79(2):127-132; Schorge J O, et al. Clin Cancer Res 2004; 10(10):3474-3478; Brakora K A, et al. Gynecol Oncol 2004; 93(2):361-365; Kim J H, et al. JAMA 2002; 287(13):1671-1679). Osteopontin mediates cell-matrix interactions and cell signaling through binding with integrin and CD44 receptors (Wai P Y, et al. J Surg Res 2004; 121(2):228-241), and is regulated by proteins in cell signaling pathways that are associated with asbestos-induced carcinogenesis. Moreover, high levels of osteopontin correlate with tumor invasion, progression, and metastases. Sandhu reported that osteopontin is upregulated in asbestos-induced tumors in a rat model of asbestos carcinogenesis and in cells treated with asbestos in vitro (Sandhu H, et al. Carcinogenesis 2000; 21(5):1023-1029).

Osteopontin refers to a secreted highly acidic glycophosphoprotein characterized by a conserved GRGDS amino acid sequence that includes, without limitation, the proteins described in Denhardt, D. T and Guo, X. FASEB J. 7:1475-82 (1993); and Denhardt, D. T. et al (Eds), "Osteopontin: Role in Cell Signalling and Adhesion," Ann. NY Acad Sci. (1995) and homologous proteins. As used herein, the term encompasses variants and fragments of osteopontin, i.e., naturally occurring forms of osteopontin that are substantially similar but nonidentical to described osteopontin in sequence and/or length and are capable of substituting for osteopontin in a specific binding interaction, as described below.

Human osteopontin has been completely sequenced and both polyclonal and monoclonal antibodies that recognize this protein are commercially available (e.g., from R&D Systems Inc., Minneapolis, Minn.; and Abcam Ltd., Cambridge, Mass.). Methods for detecting this protein have been described in the art and ELISA assays for quantitating the human protein are commercially available (Assay Designs Inc., Ann Arbor, Mich.). It is possible that the osteopontin in biological fluids and samples may be partially degraded or in a modified form due to processing by the body. For the purposes herein, it will be understood that assays for determining osteopontin levels which detect fragments of osteopontin or modified forms of osteopontin are included within the scope of the disclosure.

The results of the present study are described in the Examples. Briefly, there were no statistically significant differences in serum osteopontin levels between age-matched asbestos-exposed and unexposed subjects (30±3 ng/ml vs 20+4 ng/ml, respectively, p=0.06). Within the asbestos-exposed group, elevated serum osteopontin levels were associated with pulmonary plaques and fibrosis (56±13 ng/ml) but not with normal radiological findings (21±5 ng/ml), plaques (23±3 ng/ml), or fibrosis (32±71 g/ml), p=0.004. Serum osteopontin in the group with pleural mesothelioma was 133±10 ng/ml, and 30±3 ng/ml in the 69 asbestos-exposed subjects (p<0.001). Immunohistochemistry revealed osteopontin that was limited to tumor cells in 36/38 pleural mesotheliomas. ROC analysis of serum osteopontin levels comparing the asbestos-exposed non-malignancy group to the mesothelioma group had a sensitivity and specificity of 77.6% and 87% respectively at a cut-off of 48.4 ng/ml. Subgroup analysis comparing Stage I mesotheliomas to asbestos-exposed subjects revealed a sensitivity and specificity of 84.6% and 88.4% at a cut-off of 62.4 ng/ml. Serum osteopontin levels therefore can distinguish asbestos exposure without malignancy from asbestos exposure with pleural mesothelioma.

Thus, we found that osteopontin levels in the 69 members of the asbestos-exposed group did not differ from age matched controls, and that osteopontin levels within this group are a reflection of occupational exposure duration and of radiographic abnormalities. In contrast, as compared with the asbestos-exposed group, the osteopontin levels in serum from patients with pleural mesothelioma were significantly higher. Careful documentation of the type of exposure history was accomplished using a standardized occupational/environmental questionnaire, and B reader interpretation of the radiographs allowed classification of the asbestos-exposed population by important risk factors for pleural mesothelioma, including the duration of the exposure. A multiple regression analysis revealed that duration of exposure and radiographic findings were the most important influences on serum osteopontin levels, and that longer exposure and radiographic abnormalities were significantly associated with elevated osteopontin levels. Fibrotic changes but not pleural plaques were associated with elevated levels. The combination of radiographic findings with serum levels of osteopontin allow a practitioner or diagnostician to stratify asbestos-exposed populations with regard to risk for pleural mesothelioma; close surveillance might be indicated in workers with a long exposure history, pleural plaques and fibrosis, and an elevated serum osteopontin level.

An important result of this study is the ability of ELISA assays for osteopontin to identify early-stage pleural mesothelioma (Stage I). This finding has immediate clinical applications and industrial applicability because therapy is likely to influence survival of patients with Stage I pleural mesothelioma. Furthermore, immunohistochemistry showed that osteopontin is present in the tumor cells of pleural mesothelioma and not in the stroma, which supports the specificity of osteopontin for transformed mesothelial cells.

Osteopontin is being investigated as a biomarker in other types of cancer, so methods of detection using this protein are available in the art. Using immunohistochemistry, Coppola (Coppola D, et al. Clin Cancer Res 2004; 10(1 Pt 1): 184-190) described high staining levels in gastric, colorectal, pancreatic, lung, and ovarian carcinomas among others, and a strong correlation with pathologic stage. Schneider (Schneider S, et al. Clin Cancer Res 2004; 10(5):1588-1596) found that high tissue osteopontin levels, measured by a real time polymerase chain reaction, correlated with decreased survival in resected non small cell lung cancer. In both pancreatic cancer and breast cancer, serum osteopontin levels measured by ELISA were elevated in patients with new or progressive neoplasm (Koopmann J, et al. Cancer Epidemiol Biomarkers Prev 2004; 13(3):487-491; Martinetti A, et al. Endocr Relat Cancer 2004; 11(4):771-779).

Our data indicate that serum osteopontin levels could discriminate between asbestos-exposed persons and those with early stage pleural mesothelioma, independent of the histology of the mesothelioma. Moreover, the AUC approaching 0.9 implies that osteopontin has a positive predictive power equivalent to that of CA 125 for ovarian cancer (McIntosh M W, et al. Gynecol Oncol 2004; 95(1):9-15). Osteopontin levels, however, are also elevated in other types of cancers, including gastrointestinal, laryngeal, and urinary neoplasms, and these malignancies have been associated weakly with asbestos exposure. The hypothesis that the osteopontin level may be increased in asbestos workers who develop malignancies other than mesothelioma is being investigated. Nevertheless, based on data disclosed herein, asbestos workers with high osteopontin levels who do not appear to have a mesothelioma should be investigated to rule out other malignancies, including lung malignancies, and so elevated osteopontin can serve as a marker for asbestos-related injury that could progress to lung cancer.

In addition to being a useful molecular marker for mesothelioma, osteopontin levels can be used prognostically to assess the likelihood of relapse after therapy. Based on the data herein, the present disclosure provides a noninvasive method for detecting mesothelioma in patients and for identifying patients at high risk for mesothelioma recurrence.

Because osteopontin is secreted into bodily fluids, e.g., blood (plasma, serum), lymph, pleural effusion, urine, bile, milk, saliva, tears and others, the level of osteopontin in a patient can be detected and monitored using noninvasive procedures. A level of osteopontin in a bodily fluid, preferably blood, may be detected by any protein chemistry analytical techniques or bioassays capable of identifying and quantitating osteopontin. These methods are well-known in the art and are routinely used by those of ordinary skill in protein analysis and/or bioassay methodology. A preferred method involves the use of a binding agent that reacts with osteopontin (or with a variant or fragment thereof) in a highly selective manner. The binding agent itself may contain a reporter group (e.g., a radioisotope, a fluorescent compound, a fluorescence emitting metal of the lanthanide series, a chemiluminescent or phosphorescent molecule, a paramagnetic group, or an enzyme). Alternatively, a detecting reagent containing a suitable reporter molecule, and capable of binding the binding agent osteopontin complex, may be used (e.g., an anti-immunoglobulin, protein A, protein G). Examples of useful binding agents include antibodies, receptors, ligands or carrier molecules. Preferably, detection is carried out using immunoassay methods and immunoreagents that are well known in the art (Harlow and Lane, "Antibodies: A Laboratory Manual" Cold Spring Harbor Laboratory), 1988. Further details of assays relevant to osteopontin detection are disclosed in, for example, U.S. Patent Publication 20030044862.

The term antibody is intended to refer to intact antibody molecules and antigen-binding fragments such as Fab and F(ab') that are produced by proteolytic cleavage of intact antibodies. Monoclonal antibodies or polyclonal antibodies that are directed against one or more epitopes of osteopontin can be used in the methods described herein. Polyclonal antibodies to osteopontin can be obtained from the sera of animals that are immunized with osteopontin or from commercial sources. Monoclonal antibodies can be prepared by methods known to those skilled in the art (Kohler and Milstein, Nature 256:495-497, 1975).

Immunoassays are carried out in solution or, preferably, on a solid phase support that is capable of binding antigen or antibody. In a two-antibody sandwich type immunoassay, purified antibody is bound to a solid support and the support is contacted with the test fluid sample for sufficient time to allow the antigen in the sample (i.e., osteopontin) to bind to the antibody. After washing to remove unbound proteins, a second antibody is allowed to bind to the antigen. This antibody is labeled with a reporter group and is directed against an epitope on the antigen that differs from and is nonoverlapping with the epitope bound by the immobilized antibody. After washing, the amount of labeled second antibody bound to the solid support is measured. Either monoclonal antibodies or affinity-purified polyclonal antibodies can be used for this assay. The detection limit of the assay is typically about 0.01-0.1 ng antigen. The sensitivity of the assay can be varied by choice of a suitable label.

One suitable assay for use in the practice of this disclosure is a two-antibody sandwich type assay in which a secondary antibody is linked to an enzyme reporter group (ELISA). When exposed to its substrate, the enzyme will produce a product that can be detected by spectroscopic analysis or by another quantitative analytical method (e.g., a fluorescent, chemiluminescent, bioluminescent, phosphorescent or radiolabeled product). Suitable enzymes include, without limitation, alkaline phosphates, glucose oxidase, β-galactosidase, catalase, malate dehydrogenase, horseradish peroxidase, yeast alcohol dehydrogenase, and others.

Alternatively, the detection and quantitation of osteopontin in the fluid may be carried out using an antigen capture assay in which a subsaturating amount of unlabeled antibody (polyclonal, high affinity monoclonal or pooled monoclonal antibodies) is bound to the solid support, the sites for protein binding are blocked with a suitable blocking buffer (e.g., 3% BSA in PBS) and a fluid sample containing a fixed amount of labeled purified antigen (selected to provide sufficient signal within the linear range of binding to antibody) is added and allowed to bind to the antibody. After washing, the amount of labeled antigen is measured. The relative levels of antigen in different fluid samples can be determined, e.g., by assaying serial dilutions of each fluid sample and comparing the midpoints of the titration curves. The absolute amount of antigen in the sample can be determined by comparing the measured values with values obtained using known amounts of pure unlabeled antigen in a standard curve. The binding reaction between antibody and fluid sample containing labeled and unlabeled osteopontin is conveniently carried out in a microtiter plate. Alternatively, the binding may be carried out in solution and the complexes separated from the reaction mixture by contacting the reaction mixture with immobilized anti-immunoglobulin antibodies or proteins that are specific for an immunoglobulin, e.g., protein A or protein G.

An alternative method for detecting the level of an antigen in a fluid sample is to bind the fluid sample directly to a solid support, remove unbound proteins by washing, add an antibody specific for that antigen and allow it to bind. After removing unbound antibody by washing, the amount of antibody bound to the solid support is determined using a labeled secondary immunoreagent, e.g., a labeled anti-immunoglobulin antibody, protein A or protein G. This method is not useful if the antigen makes up a very small percentage of total proteins in the sample. For purposes of quantitation, the samples should contain similar amounts of proteins. Typically, solid supports with high protein binding capacity, e.g., nitrocellulose, are used, and both the primary and secondary antibodies are used in excess. Those of ordinary skill in the art using routine experimentation will be able to determine the optimal assay conditions required for detection of osteopontin in the samples.

Solid phase supports suitable for use in the assays will be known to those of ordinary skill in the art. These include microtiter wells, membranes, beads, magnetic beads, discs, gels, flat sheets, test strips, fibers and other configurations and types of materials that permit antigens and antibodies to be attached to the support. Attachment may be made by noncovalent or covalent means. Preferably, attachment will be made by absorption of the antibody or antigen to a well in a microtiter plate or to a membrane such as nitrocellulose. These techniques are familiar to those skilled in immunology and are well known in the art.

To determine the presence or absence of mesothelioma in a patient according to the methods of this disclosure, the level of osteopontin, detected by methods such as those disclosed herein, is typically compared to a predetermined value that is capable of distinguishing the presence of mesothelioma from non-mesothelioma sequelae of asbestos exposure in a specified patient population, for example a population with a history of asbestos exposure. The predetermined value may be an empirically determined value or range of values determined from test measurements on groups of patients with a particular class of tumor, e.g., other lung tumor. The predetermined value may allow identification of patients with any of Stage I, Stage II or Stage III mesothelioma. A predetermined value may also be of use in screening for patients having Stage I mesothelioma, and more particularly prior to appearance of symptoms in the patient. Alternatively, the predetermined value may be based on values measured in a particular patient over a period of time. The Examples below illustrate methods by which a predetermined value for serum osteopontin levels may be determined in patients with and without mesothelioma. It should be understood by those of ordinary skill in the art that such methods are routine and can be used without undue experimentation with other classes of tumors and with fluids other than serum, and are expected to be useful in human and non-human mammals.

In another suitable embodiment, the predetermined value is determined using a Receiver Operator Curve. This method may be used to arrive at the most accurate cut-off value, taking into account the false positive rate and the false negative rate of the diagnostic assay.

The assay can be performed in a flow-through or strip-test format by immobilizing the binding agent in a membrane. In a flow-through test, the sample is passed through the membrane and osteopontin contained in the sample complexes with the binding agent. A solution containing a second labeled binding agent is passed through the membrane and the amount of the detection reagent that binds to the complex is determined. In the strip test method, the membrane containing immobilized binding agent is dipped into a fluid sample from the patient. The sample migrates along the membrane through a region containing a second binding agent to the area containing immobilized binding agent. The amount of immobilized binding agent is selected to generate a visually detectable pattern when the sample contains a specified level of osteopontin. Antibodies and antigen-binding fragments are preferred for use in such assays, preferably in amounts ranging from 25 ng to about 1 ug, more preferably from about 50 ng to about 500 ng. Only very small amounts of patient samples are required for such a test. Specific examples of useful methods can be found in U.S. Pat. Nos. 5,518,869 and 5,712,172.

Nucleic acids including naturally occurring nucleic acids, oligonucleotides, antisense oligonucleotides, and synthetic oligonucleotides that hybridize to the nucleic acid encoding osteopontin, are also useful as agents to detect the presence of osteopontin in the biological samples (e.g., body fluids) of mesothelioma patients. The sequence of the human osteopontin gene has been disclosed by others. The present invention includes the use of nucleic acid sequences corresponding to the coding sequence of osteopontin and to the complementary sequence thereof, as well as sequences complementary to the osteopontin transcript sequences occurring further upstream or downstream from the coding sequence (e.g., sequences contained in, or extending into, the 5' and 3' untranslated regions) for use as agents for detecting the expression of osteopontin in biological samples obtained from human subjects, such as human sputum, bronchial lavage fluid, blood, or serum obtained from a patient at risk for development mesothelioma.

The preferred oligonucleotides for detecting the presence of osteopontin are those that are complementary to at least part of the cDNA sequence encoding osteopontin. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosphodiester linkage. Additionally, these nucleotides themselves, and/or the ribose moieties may be modified.

The oligonucleotides may be synthesized chemically, using any of the known chemical oligonucleotide synthesis methods well described in the art. For example, the oligonucleotides are prepared by using any of the commercially available, automated nucleic acid synthesizers. Alternatively, the oligonucleotides may be created by standard recombinant DNA techniques, for example, inducing transcription of the noncoding strand. The DNA sequence encoding osteopontin may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding osteopontin, oligonucleotides typically within the range of 8-100 nucleotides are preferred. Most preferable oligonucleotides for use in detecting osteopontin in urine samples are those within the range of 15-50 nucleotides.

The oligonucleotide selected for hybridizing to the osteopontin nucleic acid, whether synthesized chemically or by recombinant DNA technology, is then isolated and purified using standard techniques and then preferably labeled (e.g., with $^{35}$S or $^{32}$P) using standard labeling protocols.

The present invention also includes the use of oligonucleotide pairs in polymerase chain reactions (PCR) that are qualitative, semiquantitative, or nonquantitative to detect the expression of osteopontin in biological fluids. The oligonucleotide pairs consist of a osteopontin primer and a reverse osteopontin primer.

The presence of osteopontin in a sample of biological fluid of a patient can be determined by nucleic acid hybridization, such as but not limited to Northern blot analysis, dot blotting, microarray hybridization, Southern blot analysis, fluorescence in situ hybridization (FISH), and PCR. Chromatography, preferably HPLC, and other known assays may also be used to determine messenger RNA levels of osteopontin in a sample.

The osteopontin DNA conceivably may be found in the biological fluids inside a osteopontin-positive cancer cell that is being shed or released in the fluid under investigation.

In one aspect, the present invention contemplates the use of nucleic acids as agents for detecting osteopontin in biological fluids of patients, wherein the nucleic acids are labeled. The nucleic agents may be labeled with a radioactive label, a fluorescent label, an enzyme, a chemiluminescent tag, a calorimetric tag or other labels or tags that are discussed above or that are known in the art.

In another aspect, the present invention contemplates the use of Northern blot analysis to detect the presence of osteopontin mRNA in a sample of bodily fluid. The first step of the analysis involves separating a sample containing osteopontin nucleic acid by gel electrophoresis. The dispersed nucleic acids are then transferred to a nitrocellulose filter or another filter. Subsequently, the labeled oligonucleotide is exposed to the filter under suitable hybridizing conditions, e.g. 50% formamide, 5×SSPE, 2×Denhardt's solution, 0.1% SDS at 42EC., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of osteopontin nucleic acid present in the biological fluid of a patient.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence.

A specific example of PCR that is routinely performed by the skilled artisan to detect desired sequences is reverse transcript PCR. RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan. Other suitable methods of detecting osteopontin nucleic acid in biological samples include Northern blot analysis, dot blotting, Southern blot analysis, FISH, and PCR.

The above descriptions are exemplary only, and are not intended to limit the scope of the disclosure in any way. It is recognized that those skilled in the art will know of other types of assays that are suitable for use in measuring osteopontin, its fragments and variants.

The methods of the present disclosure are also useful for monitoring the response of a patient's mesothelioma to therapy, and for predicting the risk of relapse following therapy. With the use of the noninvasive inventive methods described herein, osteopontin levels can be followed from the time that mesothelioma is first diagnosed in a patient through various stages of therapy and following therapy to assess the likelihood of relapse. Furthermore, the pretreatment levels of osteopontin in patients with mesothelioma are useful prognostic indicators in these patients.

The present disclosure also encompasses the use of osteopontin measurements in combination with measurements of other selected cancer-related proteins such as, for example, including but not limited to PAI-1, uPA, uPAR, TF, VEGF, adrenomedullin, transforming growth factor-alpha, soluble mesothelin related peptides (SMRP), CA-125, CYFRA, and other gene products, for the diagnosis, prognosis, and therapy of cancer already discovered or in discovery phase. In this regard, microarray technology is a convenient approach, although other approaches can be used.

The diagnostic and prognostic methods herein may be used alone or in combination with other methods of detecting asbestos-related neoplasms. In some embodiments, compounds used to detect osteopontin can be combined with compounds used to detect other asbestos-related neoplasms, for example in a kit form, either together in one container or detection surface, or provided separately. For example, U.S. Pat. No. 4,569,788 discloses monoclonal antibodies for detecting non-small cell lung cancer, and U.S. Pat. No. 6,902,890 discloses methods and compositions for detecting lung cancers. Such methods and compositions can also be used in association with the present methods in order to determine if a subject has mesothelioma or another neoplasm of the lung. These methods and compositions are also of use in monitoring a patient's response to chemotherapy, and any other treatment of asbestos-related neoplasms including mesothelioma.

The disclosure also encompasses a method of assessing mesothelioma in a human patient, the method comprising assessing osteopontin in a pleural fluid, whereby an abnormally high level of osteopontin in the pleural fluid is an indication that the patient is afflicted with mesothelioma. The pleural fluid can be selected from the group consisting of pleural exudates, pleural transudates, pleural washes, pleural aspirates, and combinations thereof. The pleural fluid may be collected from a patient afflicted with pleural effusion, or from a patient suspected of exhibiting pleural effusion. The pleural fluid can be collected from the patient by thoracentesis, for example using methods know in the art.

In another aspect, the present disclosure encompasses screens for mesothelioma-related therapies based on measurement of osteopontin levels in bodily fluids of animal tumor models of mesothelioma, as known in the art.

The present disclosure includes a kit for use in carrying out the methods of this disclosure comprising at least one binding agent (and optionally a detecting agent) for detecting a level of osteopontin in a fluid sample from a patient with mesothelioma and a calibration means for comparing the level with a predetermined value or values.

The aspects of the disclosure described herein are intended for use in human and veterinary medicine.

The following examples are presented solely for illustration, and not to limit the scope of the claims.

EXAMPLES

Example 1

Patient Population

Asbestos-Exposed Group

Serum was obtained after written informed consent from 69 persons with a history of asbestos exposure and/or radiographic changes consistent with asbestosis at the Center for Occupational and Environmental Medicine, Royal Oak, Mich. from July 2004-September 2004. Entry criteria for this cohort were similar to that described by Cullen (Cullen M R, Am J Epidemiol 2005; 161(3):260-270). Asbestos exposure and its duration were documented using the ATS—Division of Lung Diseases (DLD)-78 Adult questionnaire (Ferris B G. Am Rev Respir Dis 1978; 118(6 Pt 2):1-120).

Subjects were either employed in a trade with established habitual asbestos exposure for which there is a documented increased risk of asbestos related diseases (including insulation, sheet metal work, plumbing, plasterboard application, ship fitting, ship electrical work, boiler making, or ship scaling) (Selikoff I J, et al. CA Cancer J Clin 1984; 34(1):48-56) or had occupational asbestos exposure (determined by ATS-Division of Lung Diseases (DLD)-78 Adult questionnaire) in any job or occupation and evidence of radiographic changes consistent with a diagnosis of nonmalignant asbestos-related disease. These radiographic findings included: benign pleural disease, defined as thickening or fibrotic plaques on pleural surfaces of the lung bilaterally, and/or diffuse lung scarring manifested by small irregular shadows bilaterally.

Each subject had a plain chest radiograph which was interpreted by a single trained radiologist (National Institute for Occupational Safety and Health, "B-reader") with proficiency in the classification of chest radiographs for pneumoconiosis using the International Labor Office (ILO) Classification System. The B reader specifically commented on the presence or absence of pleural changes, including plaques, and lung fibrosis. Lung fibrosis was interpreted using the International Classification of Radiographs of Pneumoconiosis (available at the ILO web site). This 12 point system classifies fibrosis by size and number of abnormal areas (0/– to 3/+) and only readings of ⅙ or greater were classified as asbestosis.

To document serum osteopontin levels in an unexposed, but similar population, we obtained serum after informed consent from 45 current (25) or former smokers undergoing screening bronchoscopy as entry criteria for a chemoprevention trial. Occupational histories were recorded on all these subjects (age 33-74 years) to document the absence of known exposure to asbestos; all these participants had normal a chest radiograph.

Of the 69 subjects in the asbestos-exposed group, 57 (83%) had an exposure in an asbestos related trade for 5 years or more, 7 (10%) had such exposure for less than five years, and 5 (7%) had radiographic abnormalities consistent with asbestos exposure but none documented by interview. The professions of the 64 participants with asbestos exposure were: foundry-iron workers (11), pipe fitters (7), building and construction (7), passive exposure in construction or from family (6), brake assembly/repair (5), boiler repair (4), vermiculite insulation exposure (4), machinist grinder (3), plumber (3), tool and die industry (2), ship builder (2), millwright (2), firefighter (2), brick maker (2), electrician (2), and asbestos remover (2). Radiographic evidence of fibrosis was seen in 23/69 (33%), and pleural plaques were found in 50/69 (73%) subjects; six participants with 5 to 37 years of exposure had no radiographic abnormalities, 53 had either plaque or fibrosis, and 10 had both plaques and fibrosis.

Pleural Mesothelioma

Serum was obtained after written informed consent from 76 patients under an approved Wayne State University Human Investigation Protocol (D1420) before cytoreductive surgery for pleural mesothelioma. The oldest serum was obtained 77 months before analysis, while the most recent was 3 months old. Asbestos exposure was documented by occupational history in 59/76 (78%) of the mesothelioma patients. All patients had complete surgical staging according to the International Mesothelioma Interest Group (IMIG) staging system (Rusch V W. Lung Cancer 1996; 14(1):1-12) (Stages I-13, 11-20; III-43), and were followed with computerized tomography of the chest every three to four months until death. Tumors were classified as epithelial (50), sarcomatoid (4), or mixed (22). Table 1 lists characteristics of the asbestos exposed and mesothelioma groups.

TABLE 1

Demographics of Mesothelioma and Asbestos Exposed Populations

|  | Malignant Pleural Mesothelioma (76) | Asbestos-Related Nonmalignant Disease (69) |
| --- | --- | --- |
| Age, years (mean + standard error) | 65 + 1 | 65 + 1 |
| Sex | 60 Male/16 Female | 61 Male/8 Female |
| Ethnicity | 72 Caucasian/4 African-American | 66 Caucasian/3 African-American |
| Smoking History | 60 Smoker/16 Non-smoker | 56 Smoker/13 Non-smoker |

Statistical Analyses

Kaplan Meier survival plots and log rank tests were used to assess differences in survival for the pleural mesothelioma patients. The ability of serum osteopontin levels to distinguish the pleural mesothelioma group from the asbestos-related group was evaluated by descriptive statistics, and by Receiver Operating Characteristic (ROC) curves (Metz C E. Semin Nucl Med 1978; 8(4):283-298; Zweig M H, et al. Clin Chem 1993; 39(4):561-577). The area under the ROC curve (AUC) was calculated, and 95% confidence intervals used to test the hypothesis that the theoretical area is 0.5. An AUC whose confidence interval did not include the 0.5 value was considered evidence that the laboratory test had some ability to distinguish between the mesothelioma and asbestosis-exposed groups (Zweig M H, et al. Clin Chem 1993; 39(4):561-577; Hanley J A, et al. Radiology 1982; 143(1):29-36). Differences between groups were calculated using ANOVA and by multiple regression analysis in stepwise fashions entering only variables that were $p<0.05$ in the model. All statistical analyses were performed using MedCalc Software, Mariakerke, Belgium.

Example 2

Survival by Stage of Pleural Mesothelioma

Figure 1B:
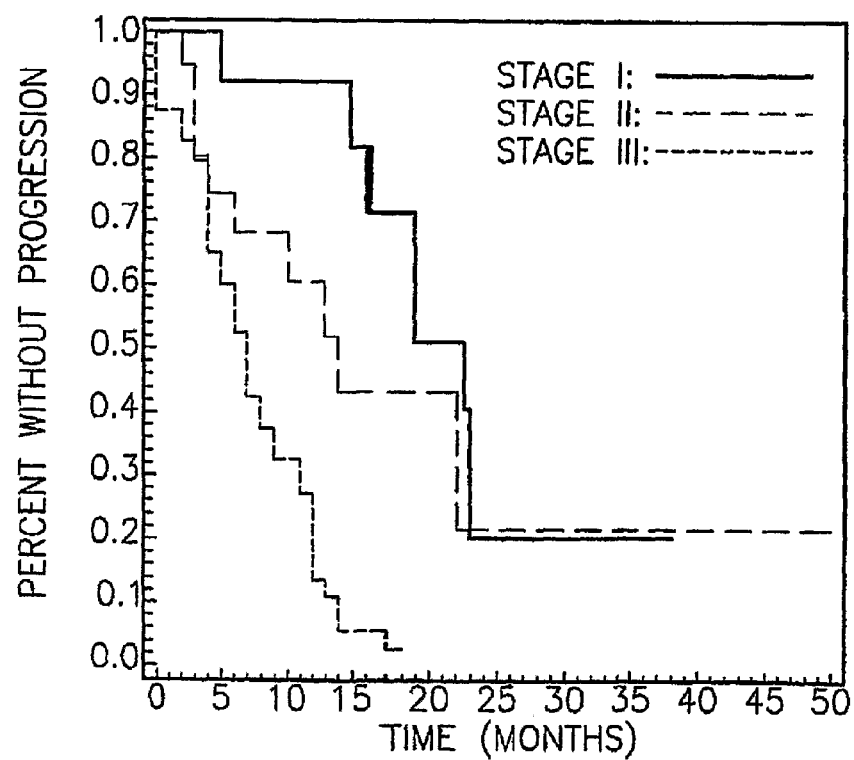

To determine whether the mesothelioma patients in this study had outcomes similar to those in other series, survival and time to progression curves based on IMIG staging status were generated. FIG. 1 shows significant differences in survival and progression according to stage as follows: (A) median survivals for the 13 Stage I, 20 Stage II, and 40 Stage III patients were 32, 19, and 13 months, respectively, p=0.006 by log rank test; (B) median time to progression for the 13 Stage I, 20 Stage II, and 40 Stage III patients were 23, 14, and 7 months, respectively, p<0.001 by log rank test. These results are consistent with those of other studies that used the IMIG staging system (Pass H I, et al. J Thorac Cardiovasc Surg 1998; 115(2):310-317; Rusch V W, et al. Ann Thorac Surg 1999; 68(5):1799-1804; Rusch V W, et al. J Thorac Cardiovasc Surg 1996; 111(4):815-825).

Example 3

Immunohistochemistry

Immunohistochemistry was performed on a multi-tissue pleural mesothelioma array, consisting of 2-mm representative areas of resected tumor and normal tissue controls. Thirty-eight of the 76 pleural tumors studied for serum osteopontin were spotted on the array. The other 38 were not available at the time of array construction. Immunohistochemistry was performed using the standard ABC technique. The primary antibody, a monoclonal anti-osteopontin antibody (clone OP3N, Vector Laboratories, Burlingame, Calif.), was applied to the array at 1:150 dilution, for 90 minutes at room temperature. The secondary anti mouse IgG (Vector Laboratories, Burlingame, Calif.) was applied at 1:200 dilution for 30 minutes at room temperature. A positive control, and a negative control (obtained by omitting the secondary antibody) were included in each run. Cases were scored separately for (1) intensity (I) (scale of 1 to 3) and (2) extent (E) of positive tumor cells ($1 \leqq 10\%$; $2=\geqq 10$ and $\leqq 50\%$; $3=\geqq 50\%$).

Figure 2:
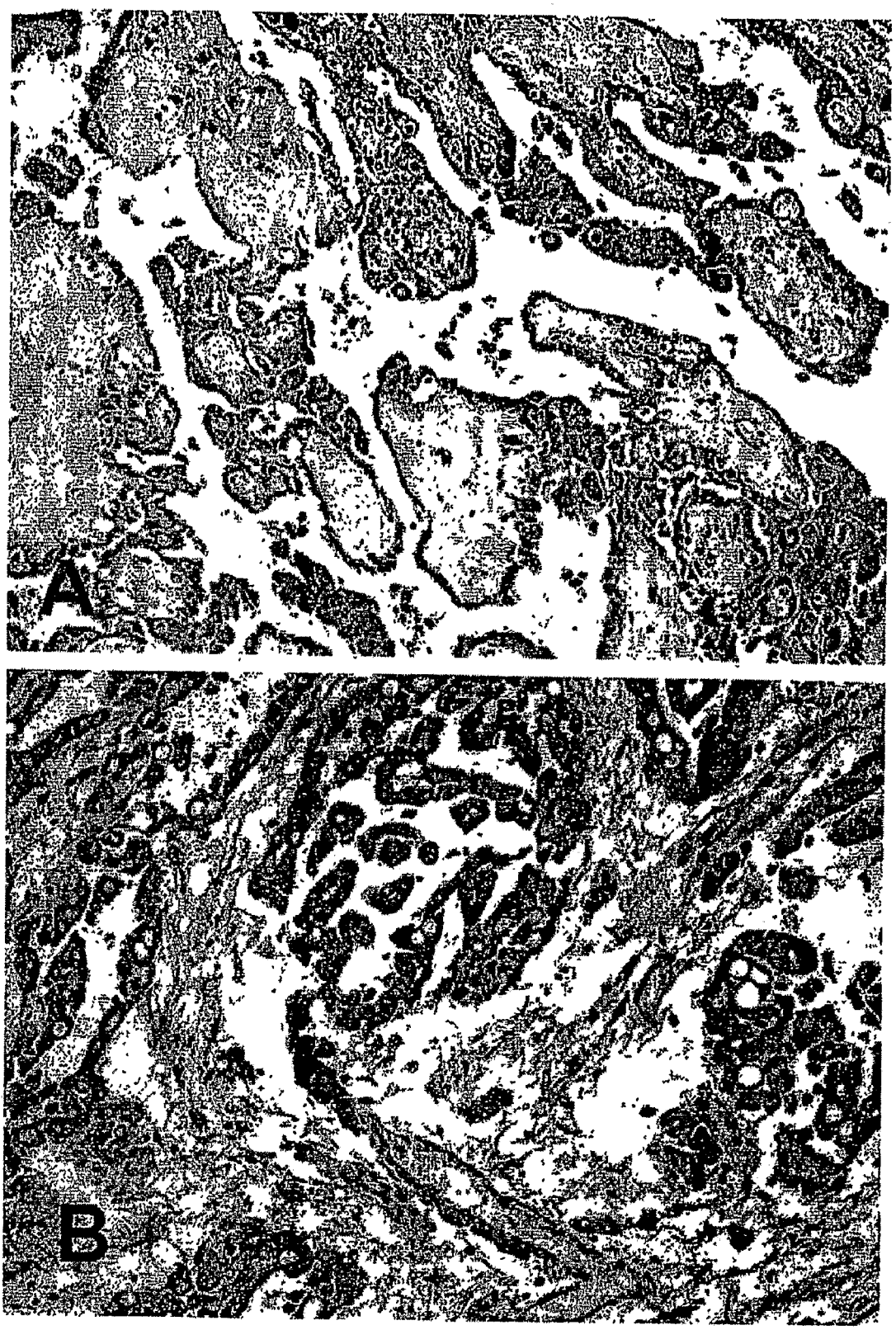
FIG. 2A is a photograph illustrating osteopontin immunohistochemistry in pleural mesotheliomas at magnification× 100.
FIG. 2B is a photograph illustrating osteopontin immunohistochemistry in pleural mesotheliomas at magnification× 400.

Of the tumor tissue available for osteopontin staining (from 38 of the 76 mesotheliomas), 36 of the 38 were positive for osteopontin (FIG. 2). They showed cytoplasmic staining in $\geqq 50\%$ of tumor cells, and staining intensity ranged from 1 to 3 (13=1; 8=2; 15=3). Osteopontin was seen in all pleural mesothelioma variants (epithelial, 19/20; biphasic 15/16; and sarcomatoid 2/2). Lung parenchyma and adjacent normal pleura were negative; fibroblasts in tumor-associated stroma were infrequently weakly positive; the media and intima of vessels showed weak positivity. In FIG. 2A, magnification was ×100; in FIG. 2B, magnification was ×400.

Example 4

ELISA Assay for Osteopontin

For osteopontin ELISA, the Human Osteopontin Assay Kit (IBL Company, LTD., Gunma, Japan) was used to determine the level of serum osteopontin; all samples were coded. Each specimen was tested in duplicate and the results quantitated in ng/ml using a standard curve.

Asbestos-Exposed and Unexposed Groups

Figure 3A:
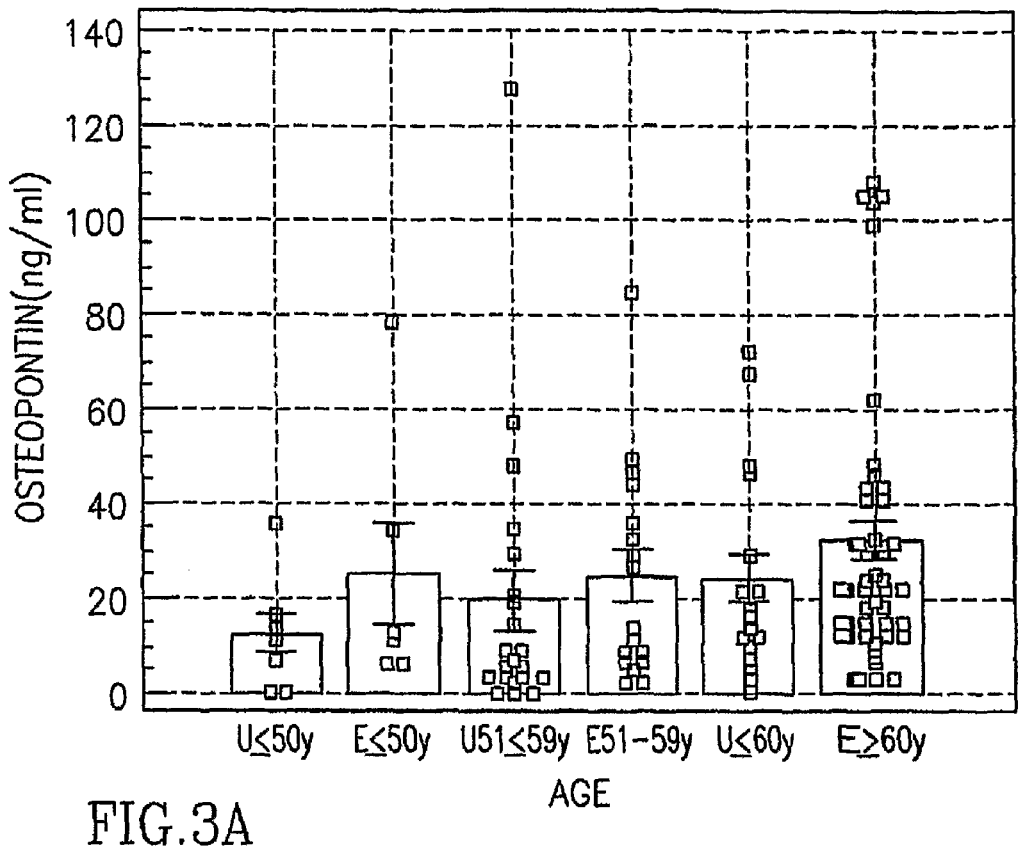
FIGS. 3A-3D are bar graphs that illustrate the influence of asbestos demographics on serum osteopontin levels.
Figure 3B:
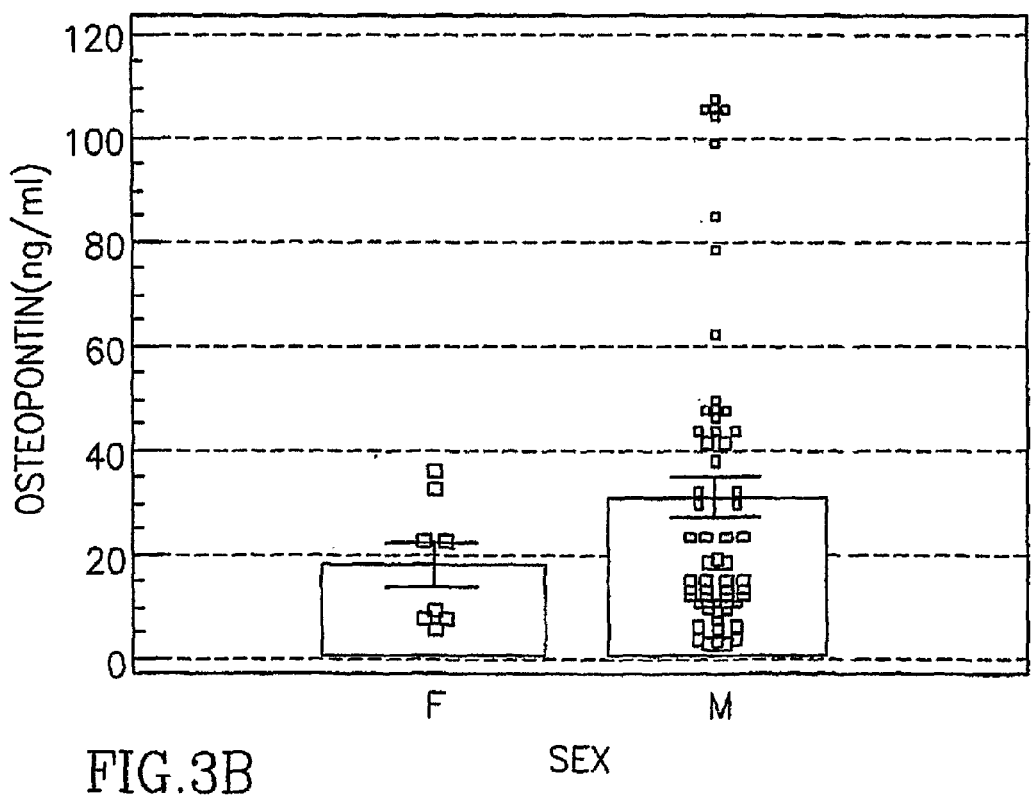

The mean serum level of osteopontin in the entire asbestos-exposed group was 30±3 ng/ml (range 2-221 ng/ml, 95% Confidence Interval (CI)=23.1 to 36.1 ng/ml). The levels in age-matched unexposed controls with normal radiographs did not differ from those measured for the asbestos exposed group (age<50: 12±5 ng/ml vs. 25±11 ng/ml, respectively, 95% CI of difference −16 to 41 ng/ml, p=0.34; age 50-60: 19±6 ng/ml vs 24±5 ng/ml, respectively, 95% CI of difference −12 to 22 ng/ml, p=0.56; age>60, 24±5 ng/ml vs 32±4 ng/ml, respectively, 95% CI of difference −23 to 7, p=0.29 (FIG. 3A). For the asbestos-exposed cohort, there were no significant differences in osteopontin levels according to sex or the presence or absence of pleural plaques (p=0.19, and p=0.88, respectively; FIGS. 3B, D).

Figure 3C:
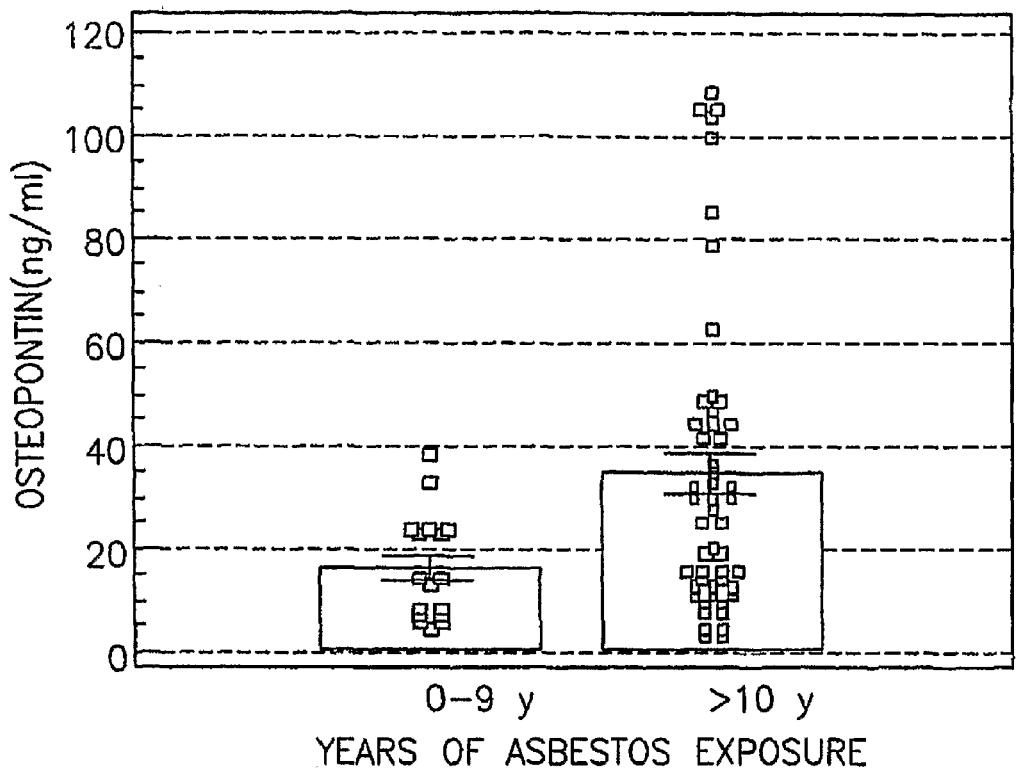
Figure 3D:
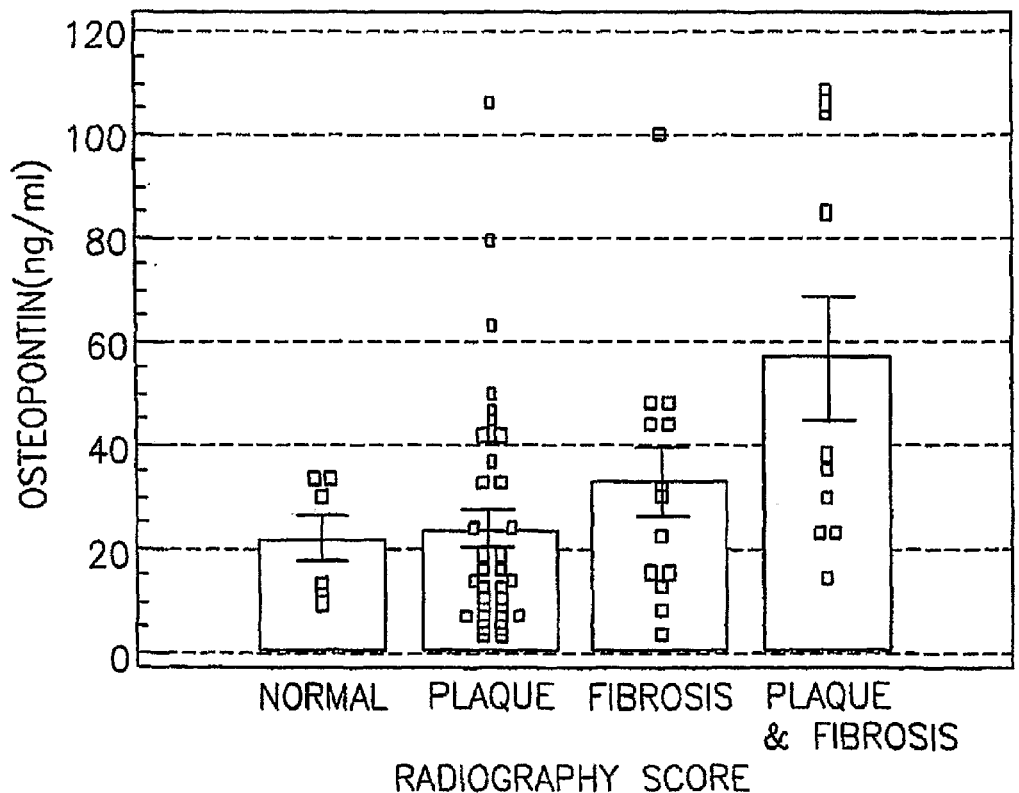
Figure 4A:
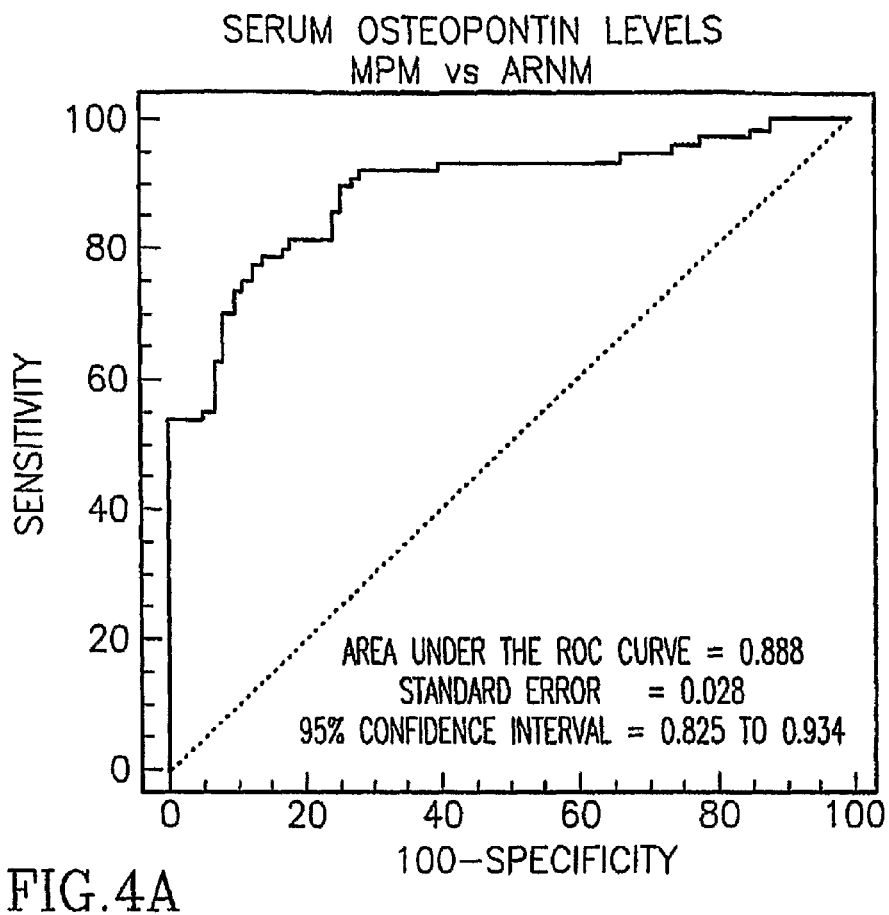
FIGS. 4A-F are graphs illustrating the ROC (Receiver Operating Characteristics) curves for mesothelioma versus asbestos exposed populations.
Figure 4B:
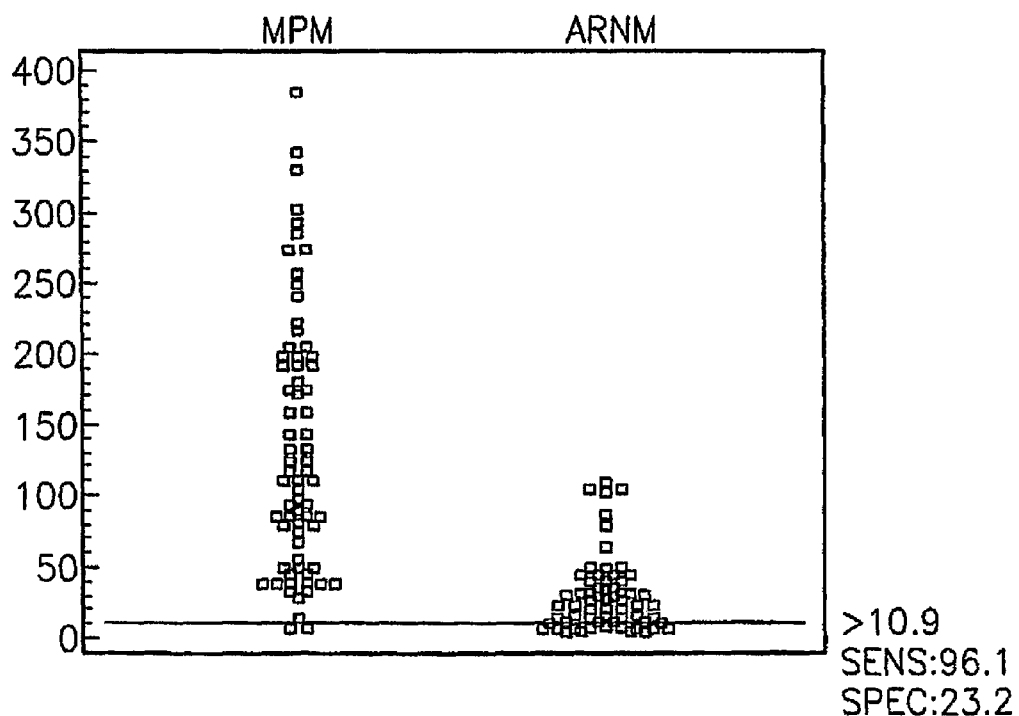
Figure 4C:
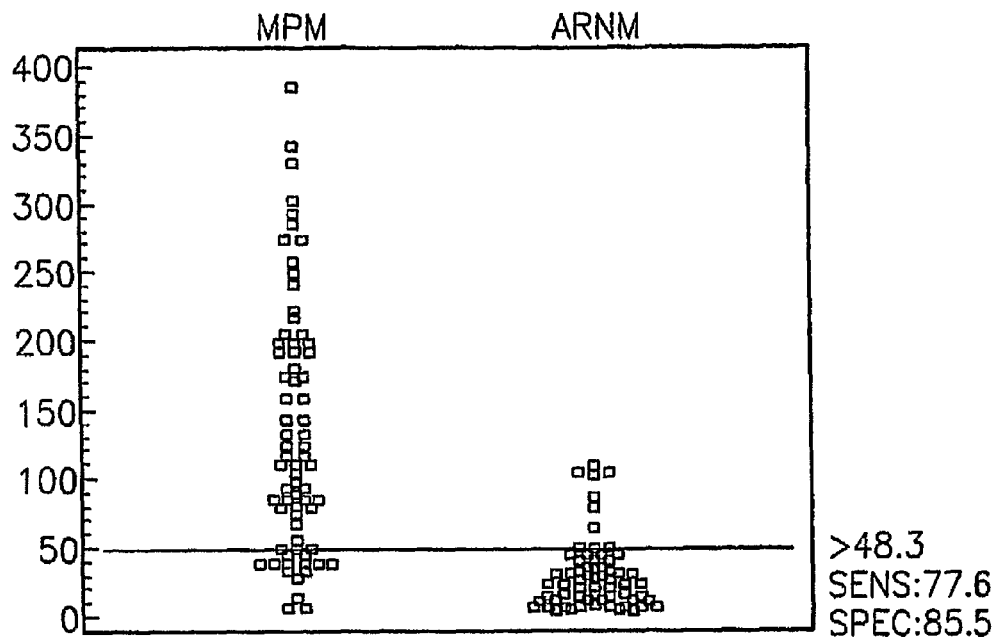
Figure 4D:
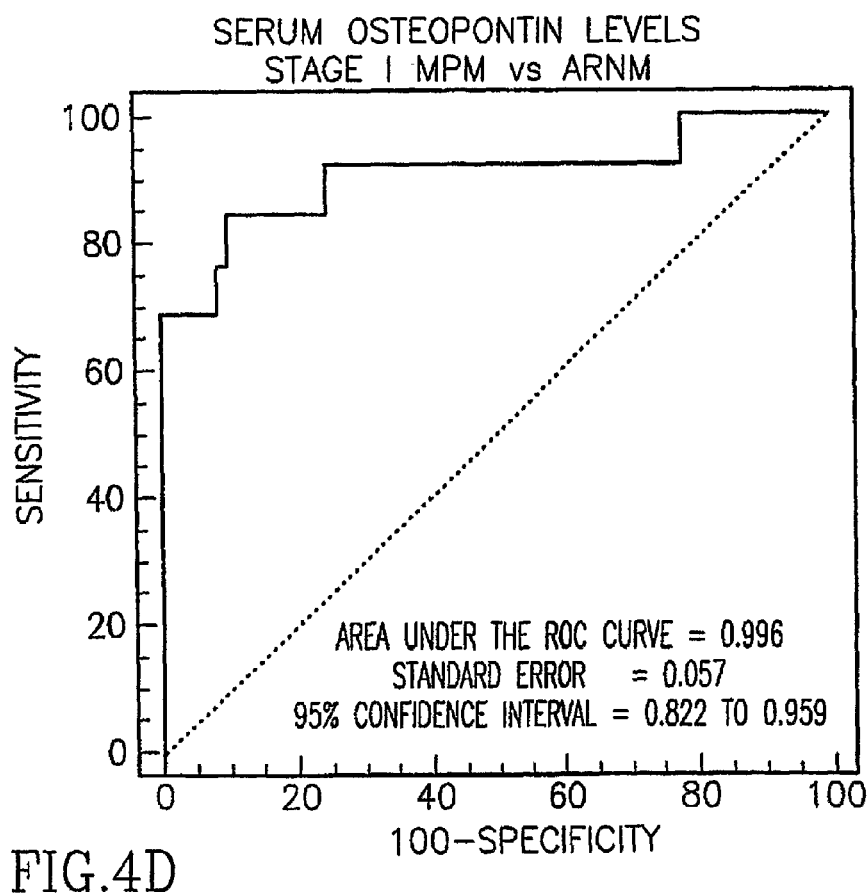
Figure 4E:
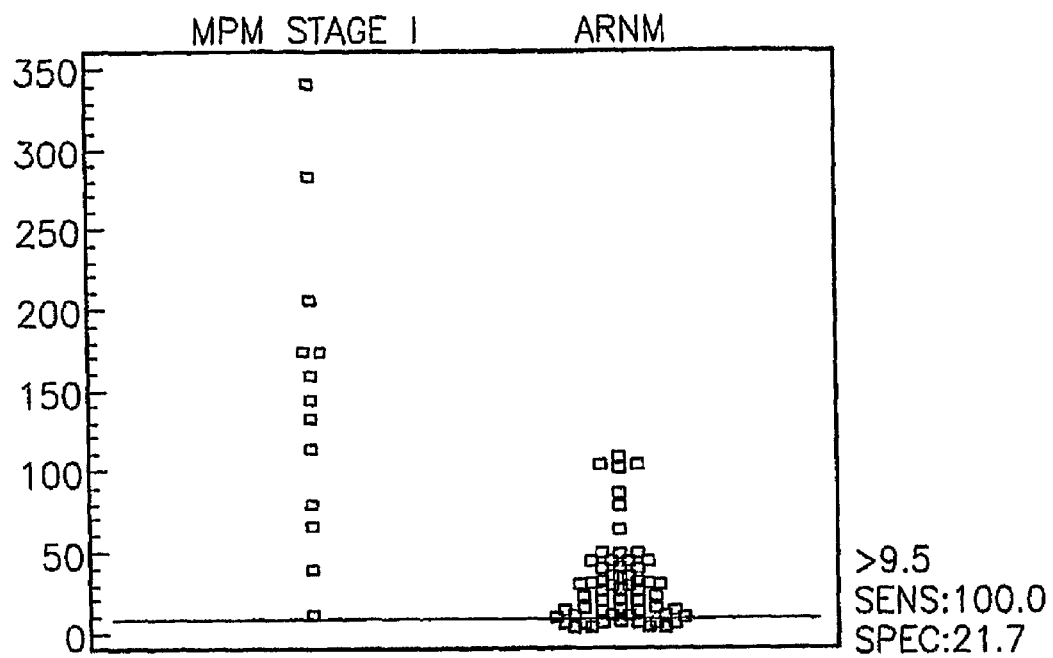
Figure 4F:
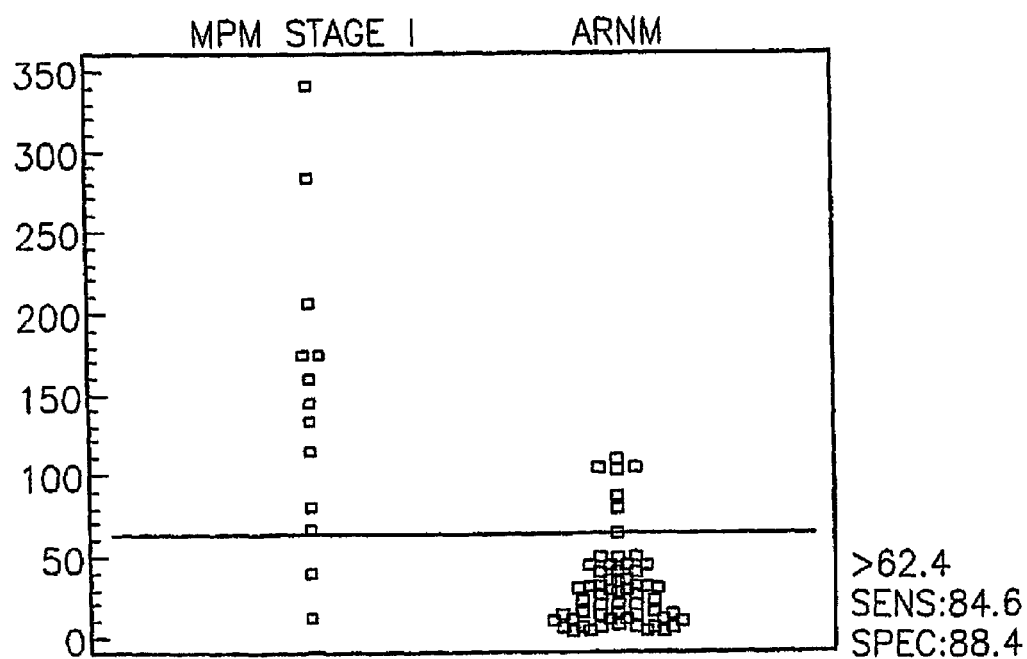

The subgroup with lung fibrosis had a significantly higher mean level of osteopontin than the subgroup without fibrosis (43 ng/ml vs. 23 ng/ml, respectively, 95% CI of difference 7 to 33 ng/ml. p=0.004), and the mean levels were significantly higher with 10 or more years of exposure (34 ng/ml vs. 16 ng/ml, respectively, 95% CI of difference 4 to 33 ng/ml, p=0.015, FIG. 3C). The highest levels of serum osteopontin were found in subjects who had both plaques and fibrosis (56±13 ng/ml).

When serum osteopontin levels for age matched unexposed controls (age, 64±3 years) were compared to asbestos exposed subjects with plaques and fibrosis (age, 64±3 years), significant differences in osteopontin levels were noted (14±6 ng/ml vs. 56±13 ng/ml, p=0.03). Asbestos exposed subjects with a normal chest radiograph (21±5 ng/ml), plaques (23±3 ng/ml), or fibrosis (32±7 ng/ml) also had significantly lower osteopontin levels than those with plaques and fibrosis (p=0.004). A multiple regression analysis that included age, duration of asbestos exposure, presence of fibrosis, presence of plaques, and the International Labor Organization radiography score was performed. Only the duration of asbestos exposure (p=0.001) and the radiography score (p<0.001) were independently associated with osteopontin levels, with zero order correlation coefficients of 0.357 and 0.399 respectively.

Pleural Mesothelioma

The mean serum osteopontin level in the mesothelioma group, 133±10 ng/ml (range 6-385 ng/ml, 95% confidence interval 113-154 ng/ml), was significantly different from the mean in the asbestos-exposed group (30±3 ng/ml, range 2-221 ng/ml, 95% CI=23.1 to 36.1 ng/ml, p<0.001). There were no significant differences in mean serum osteopontin levels in Stage I (147±26 ng/ml, range 10-341 ng/ml, 95% CI 92-204 ng/ml), stage II (158±22 ng/ml, range 14-385 ng/ml, 95% CI 99-216 ng/ml)), or stage III (118±12 ng/ml, range 4-302 ng/ml, 95% CI 83-145 ng/ml) mesothelioma (P=0.15, Stage II vs. Stage III); however, the means in all these stages differed significantly from the mean of the asbestos-exposed group (30±3 ng/ml, range 2-221 ng/ml, 95% CI=23.1 to 36.1 ng/ml, p<0.001). Moreover, when serum osteopontin levels for the asbestos exposed subjects with plaques and fibrosis were compared with levels from the pleural mesothelioma group, the levels were significantly different (56±13 ng/ml vs 133±10 ng/ml, respectively, 95% CI of difference=49 to 114 ng/ml, p<0.0001). Mean osteopontin levels were similar in men and women with mesothelioma (136±12 ng/ml vs. 125±21 ng/ml, respectively; 95% CI of difference=−61 to 39 ng/ml, p=0.6575) and did not vary by tumor histology (epithelial, 128±13 ng/ml vs. non-epithelial, 133±18, 95% CI of difference=−28 to 59 ng/ml, p=0.49) or history of asbestos exposure (exposed 151±24 ng/ml vs. unexposed 128±12 ng/ml, 95% CI of difference=−73 to 28 ng/ml, p=0.37).

Example 5

Receiver Operating Characteristic Curves

ROC analyses comparing the asbestos exposed subjects to the pleural mesothelioma patients had an area under the curve (AUC) of 0.888 (95% CI 0.825 to 0.934) (FIG. 4).

The six panels of FIG. 4 are as follows: (A) All 76 mesotheliomas versus 69 asbestos exposed, Area Under Curve (AUC) =0.888. (B) High sensitivity for early detection of mesothelioma at a cutoff level of 10.9 ng/ml. (C) Cut-off for minimization of total classification error was level >48.4 ng/ml. (D) Stage I mesotheliomas versus asbestos exposed subjects, AUC=0.906. (E) High sensitivity for early detection of Stage I mesothelioma versus asbestos exposed subjects at cutoff level of 9.5 ng/ml. (F) Cut-off for minimization of total classification error for Stage I versus asbestos exposed was a level >62.4 ng/ml.

Subgroup analyses revealed AUCs for Stage I, Stage II, Stage I/II, and Stage III pleural mesothelioma, compared with asbestos controls, to be 0.906, 0.925, 0.917, and 0.865, respectively. A cut-off of 48.4 ng/ml (sensitivity and specificity of 78% and 87%) had the highest accuracy (minimal false negative and false positive) for confirming mesothelioma from the asbestos exposed cohort without mesothelioma. For the purpose of screening, i.e. early detection for mesothelioma, a cutoff with the highest (95-99 percent) sensitivity might be most appropriate independent of specificity, and at a cutoff of 10.9 ng/ml, the sensitivity for osteopontin level was 96.1% with a specificity of 23.2%. If screening were for detection of Stage I disease only, a cutoff of 9.5 ng/ml gave 100% sensitivity with 20.3% specificity. The most accurate cutoff, however, for the detection of a Stage I mesothelioma (sensitivity of 84.6% and specificity of 88.4%) was with a cut-off of 62.4 ng/ml.

All references cited herein are fully incorporated by reference. Having now fully described the disclosure, it will be understood by those of skill in the art that the disclosure may be performed within a wide and equivalent range of conditions, parameters and the like, without affecting the spirit or scope of the disclosure or any embodiment thereof.

What is claimed:

1. A method of diagnostically evaluating whether a human subject is at risk of having pleural mesothelioma, comprising: (a) obtaining a biological sample from said subject; (b) assaying said sample for the concentration of osteopontin present; (c) comparing the results obtained from the assay of step (b) with results obtained from the assay of one or more control samples wherein said one or more control samples are obtained from asbestos-exposed subjects; and (d) concluding that said subject is at increased risk of having pleural mesothelioma if the concentration of osteopontin in said subject sample is higher than the concentration in said control sample or samples.

2. The method of claim 1, wherein the concentration of osteopontin present in said samples is determined by an immunoassay.

3. The method of claim 1, wherein the concentration of osteopontin in said sample is determined using an ELISA.

4. The method of claim 1, wherein said biological sample is serum.

5. The method of claim 1, wherein it is concluded that a subject is at increased risk of having pleural mesothelioma if the osteopontin concentration in said subject sample is higher than the amount in said control sample or samples by a predetermined value.

6. The method of claim 1, further comprising performing at least one additional assay for a diagnostic marker of cancer.

7. The method of claim 6, wherein said cancer is non-mesothelioma asbestos-related lung cancer.

8. A method of assessing the likelihood that a human patient will develop pleural mesothelioma, the method comprising assessing the amount of osteopontin in a sample obtained from the patient and comparing that amount with a reference value derived from one or more reference humans of known pleural mesothelioma outcome wherein reference humans have been exposed to asbestos, whereby a higher amount of osteopontin in said patient is indicative of the likelihood that the patient will develop pleural mesothelioma.

9. The method of claim 8, wherein the sample comprises serum.

* * * * *